(12) United States Patent
Blair et al.

(10) Patent No.: US 9,599,592 B2
(45) Date of Patent: Mar. 21, 2017

(54) METHOD AND APPARATUS FOR MAGNETIC CRACK DEPTH PREDICTION

(76) Inventors: Ian Stewart Blair, North Perth (AU); Stephanie Klecha, Surrey (GB); Lloyd Lissiman, Floreat (AU)

(*) Notice: Subject to any disclaimer, the term of this patent is extended or adjusted under 35 U.S.C. 154(b) by 898 days.

(21) Appl. No.: 13/583,624

(22) PCT Filed: Mar. 10, 2011

(86) PCT No.: PCT/AU2011/000270
§ 371 (c)(1),
(2), (4) Date: Jan. 23, 2013

(87) PCT Pub. No.: WO2011/109869
PCT Pub. Date: Sep. 15, 2011

(65) Prior Publication Data
US 2013/0113472 A1    May 9, 2013

(30) Foreign Application Priority Data
Mar. 10, 2010  (AU) ................................ 2010900993

(51) Int. Cl.
*B61K 9/10* (2006.01)
*G01N 27/83* (2006.01)
*G01N 27/82* (2006.01)

(52) U.S. Cl.
CPC ............. *G01N 27/83* (2013.01); *G01N 27/82* (2013.01)

(58) Field of Classification Search
CPC ........ G01N 27/82; G01N 27/72; G01N 27/83; G01N 17/006; G01N 27/9013; G01N 27/902; G01N 27/9026; G01N 27/904; G01N 27/9046; H02K 1/2766; H02K 1/02;
(Continued)

(56) References Cited

U.S. PATENT DOCUMENTS

| 4,727,321 A | * | 2/1988 | Huschelrath | ........... G01N 27/82 324/226 |
| 5,336,998 A | * | 8/1994 | Watts | ..................... G01N 27/82 324/235 |

(Continued)

FOREIGN PATENT DOCUMENTS

| CN | 1641347 | 7/2005 |
| CN | 101458227 A | * 6/2009 |

(Continued)

OTHER PUBLICATIONS

PCT/AU2011/000270, Oct. 9, 2012, International Preliminary Report on Patentability—CH II. (pp. 3-4).*
(Continued)

*Primary Examiner* — Jermele M Hollington
*Assistant Examiner* — Sean Curtis
(74) *Attorney, Agent, or Firm* — Ladas & Parry, LLP (57) ABSTRACT

A method of magnetic crack depth prediction for a magnetisable component of a first geometry comprising determining a measure of remnant magnetic flux leakage for a section of the component, and converting the remnant magnetic flux leakage to a predicted crack depth for that section of the component using an empirically determined relationship between remnant magnetic flux leakage and crack depth for a previously tested in service component of the first geometry.

25 Claims, 10 Drawing Sheets

(58) Field of Classification Search
CPC .... H01F 3/04; B61K 9/10; G01L 23/223; G01R 33/10
USPC ............. 324/216–217, 220–221, 228, 235, 324/237–238, 242, 251, 260, 262–263; 702/35, 38
See application file for complete search history.

(56) References Cited

U.S. PATENT DOCUMENTS

| | | | | |
|---|---|---|---|---|
| 5,408,178 | A * | 4/1995 | Wikswo, Jr. | G01R 33/16 324/201 |
| 5,479,100 | A * | 12/1995 | Fowler | G01N 27/83 324/220 |
| 5,804,964 | A * | 9/1998 | Hamelin | G01N 27/82 324/227 |
| 6,037,767 | A * | 3/2000 | Crescenzo | G01N 27/82 324/220 |
| 6,549,005 | B1 * | 4/2003 | Hay | G01N 27/82 324/217 |
| 7,256,576 | B2 * | 8/2007 | Mandziuk | F16L 55/40 324/220 |
| 7,403,000 | B2 * | 7/2008 | Barolak | E21B 47/082 324/221 |
| 7,526,971 | B2 * | 5/2009 | Mandziuk | F16L 55/38 73/866.5 |
| 7,899,628 | B2 * | 3/2011 | Duckworth | G01M 5/0025 702/38 |
| 2004/0041560 | A1 * | 3/2004 | Walters | G01N 27/82 324/238 |
| 2004/0058823 | A1 * | 3/2004 | Backer | H01L 39/2464 505/100 |
| 2004/0100256 | A1 | 5/2004 | Fickert et al. | |
| 2006/0219011 | A1 * | 10/2006 | Siddu | G01N 29/0645 73/597 |
| 2007/0222436 | A1 * | 9/2007 | Gao | G01N 27/82 324/220 |
| 2007/0250277 | A1 * | 10/2007 | Hagit | G01N 27/20 702/64 |
| 2007/0261186 | A1 * | 11/2007 | Batzel | A46B 3/08 15/104.061 |
| 2008/0258719 | A1 * | 10/2008 | Putman | G01N 27/87 324/240 |
| 2009/0164143 | A1 * | 6/2009 | Duckworth | G01M 5/0025 702/38 |
| 2009/0234590 | A1 * | 9/2009 | McNealy | G01N 27/82 702/38 |
| 2010/0042336 | A1 * | 2/2010 | Lee | G01N 27/9006 702/38 |
| 2010/0084322 | A1 * | 4/2010 | Johnson | B07C 5/342 209/552 |
| 2010/0163433 | A1 * | 7/2010 | Horn | G01N 27/20 205/790.5 |
| 2010/0199767 | A1 * | 8/2010 | Ganin | G01N 29/225 73/623 |
| 2013/0113472 | A1 * | 5/2013 | Blair | G01N 27/83 324/217 |

FOREIGN PATENT DOCUMENTS

| | | | | |
|---|---|---|---|---|
| CN | 101520433 | | 9/2009 | |
| EP | 1995589 | | 11/2008 | |
| GB | WO 2009063218 | A2 * | 5/2009 | ............ F17D 5/00 |
| JP | 63-205558 | | 8/1988 | |
| JP | 5-196581 | | 8/1993 | |
| JP | 2001-194344 | | 7/2001 | |
| JP | 2001194344 | A * | 7/2001 | |
| JP | 2003-43015 | | 2/2003 | |
| JP | 2003294708 | A * | 10/2003 | |
| JP | 2004-37216 | | 2/2004 | |
| WO | 2009/063218 | | 5/2009 | |
| WO | WO 2009063218 | A2 * | 5/2009 | ............ G01N 17/02 |
| WO | 2009/110795 | | 9/2009 | |

OTHER PUBLICATIONS

ISR and IPRP for PCT/AU2011/000270 mailed on Apr. 12, 2011 and Aug. 5, 2011.

Australian Patent Office International-Type Search Report for Australian Application No. 2010900993 mailed on Dec. 9, 2010.

PCT Written Opinion of the ISA from PCT/AU2011/000270 dated Apr. 12, 2011.

* cited by examiner

METHOD AND APPARATUS FOR MAGNETIC CRACK DEPTH PREDICTION

CROSS-REFERENCE TO RELATED APPLICATIONS

This application is the U.S. National Stage of International Patent Application No. PCT/AU2011/000270 filed on Mar. 10, 2011, which claims priority to Australian Patent Application No. 2010900993 filed on Mar. 10, 2010, the disclosures of which are hereby incorporated by reference in their entireties.

FIELD OF THE INVENTION

The present invention relates to a method and apparatus for magnetic crack depth prediction of components such as, but not limited to, rail way tracks, rail wheels, and steel beams.

BACKGROUND OF THE INVENTION

Components and structures which are subject to dynamic loading may be monitored for fatigue damage. This damage is sometimes evidenced by surface breaking cracks. Monitoring for fatigue damage is often important to maintain safety for people and equipment which use or operate in or on a multitude of engineered structures such as bridges, buildings, aircraft and rail transport systems. In the rail transport environment for example, rolling contact fatigue (RCF) is a major cause of rail track and rail wheel damage. There are several types of RCF damage including cracking, spalling and squats. Cracking is typically manifested by a continuous band of fine cracks that initiate in the gauge corner of a head of the rail. Spalling is characterised by small pieces of the rail head breaking away from the surface where RCF cracks have coalesced. Squats are subsurface voids that are not visible on the rail surface but become visible when the rail surface is milled away.

In the rail environment, RCF is a result of repeated overstressing of the surface or subsurface material of a rail track or wheel as a result of repeated wheel-rail contact cycles.

It is common in the maintenance of rail tracks to periodically grind or mill the running surface of a rail track to remove or at least decrease the depth of cracks and defects in the track surface to thereby extend the service life of the rail track and avoid catastrophic failure. To avoid grinding and milling the entire rail track in a rail network various non-destructive testing techniques are used to detect the existence of cracks. Examples of non-destructive testing techniques include ultrasonic testing, magnetic testing, eddy current systems, and differential pressure crack monitoring systems. These techniques are not limited to use in a rail environment and are used for testing of other load bearing components or structures made of a magnetisable material. In many situations, the mere existence of a crack is not in itself of major concern. It is other characteristics of the crack that trigger maintenance or corrective procedures for a load bearing component or structure. One of these characteristics is crack depth. For example, the existence of multiple shallow surface cracks may not require any action whereas a single deep crack may require immediate action.

SUMMARY OF THE INVENTION

One aspect of the invention provides a method of magnetic crack depth prediction for a magnetisable component of a first geometry comprising:

determining a measure of remnant magnetic flux leakage for a section of the component; and, converting the remnant magnetic flux leakage to a predicted crack depth for that section of the component using an empirically determined relationship between remnant magnetic flux leakage and crack depth for a previously tested in service component of the first geometry.

A second aspect of the invention provides a 0 method of magnetic crack depth prediction for a magnetisable component comprising:

determining a measure of remnant magnetic flux leakage for a section of the component; and, using the determined remnant magnetic flux leakage to calculate a damage index representative of a predicted crack depth for that section of the component.

In the second aspect the method may further comprise:

empirically determining a relationship between damage index and crack depth and utilising this relationship to predict crack depth for a calculated damage index.

Determining remnant magnetic flux leakage may comprise:

obtaining at least one signal representative of remnant magnetic flux leakage along the section of the component and processing the at least one signal to determine remnant magnetic flux leakage.

The methods may comprise applying a magnetic field in one direction along the section of the component to produce the remanent magnetic field in the section of the component and wherein the at least one signal is representative of magnetic flux leakage from the remanent magnetic field.

Obtaining the at least one signal may comprise obtaining a plurality of signals for mutually adjacent strips of the section of the component where the strips extend transverse to the direction of application of the magnetic field.

Processing the at least one signal may comprise filtering the at least one signal.

Filtering the at least one signal may comprise filtering the at least one signal through a high pass filter to remove signal components having a wavelength greater than a first wave length.

Filtering the at least one signal may comprise passing the at least one signal through a digital high pass filter in opposite directions.

The filtering may further comprise passing the at least one signal through a low pass filter to remove signals of a wavelength less than a second wave length.

In one embodiment the at least one signal is passed through the low pass filter prior to passing through the high pass filter.

Processing the at least one signal may further comprise conditioning the signals on the basis of distance between the or each sensor and an underlying surface of the component.

Conditioning the signal may comprise multiplying the or each signal by a factor:

$$\frac{1}{\frac{1}{\pi}\left[\text{ArcTan}\left(\frac{AB}{2H\sqrt{A^2+B^2+4H^2}}\right) - \text{ArcTan}\left(\frac{AB}{2(H+C)\sqrt{A^2+B^2+4(H+C)^2}}\right)\right]}$$

where A, B and C are constants dependant on the geometry of the component and H is the perpendicular distance of the or each sensor from the underlying surface of the component.

Processing the at least one signal may further comprise analysing the or each signal and providing an indication of major damage to the section of the component when the signals have characteristics of low frequency and high amplitude.

Providing an indication of major damage may comprise subsequent to the high pass filtering, calculating respective sums of data points from the high pass filtered signals above and below respective positive and negative thresholds for all of the sensors, comparing the sums with respective pre-calculated severe damage indicators, and reporting the existence of major damage when either sum exceeds the respective pre-calculated severe damage indicator.

Processing may further comprise calculating a maximum peak to peak amplitude for the or each filtered signal for the section of the component.

Processing may further comprise integrating the peak to peak amplitude for the or each signal for the section of the component to provide the measure of remnant magnetic flux leakage for the section of the component.

DETAILED DESCRIPTION OF THE PREFERRED EMBODIMENT

Embodiments of the present invention are derived from extensive observation and testing by Applicant which indicates a relationship between crack depth and magnetic flux leakage from a crack in a magnetisable material. The term "magnetisable material" is used throughout this specification including the Claims to denote materials in which magnetism can be induced and a remnant magnetic field maintained for a period of time after the application and subsequent removal of an inducing magnetic field. The relationship between crack depth and magnetic flux leakage is empirically determined for a component of a particular geometry. Embodiments of the present method comprise determining total magnetic flux leakage for a section of a component and, utilising the empirically determined relationship between magnetic flux leakage and crack depth to convert the total magnetic flux leakage to a predicted crack depth for that section of the component.

The empirical relationship may be represented by a mathematical equation, a graph or a look up table. The total magnetic flux leakage for a section of the component is referred to as a "damage index". When the empirical relationship is represented graphically in a 2D co-ordinate system, the damage index, which is a positive number, may be graphed along the Y axis, while crack depth may be graphed along the X axis.

When embodiments of the method are applied to a rail track, at least one but preferably a plurality of signals representative of magnetic flux leakage are obtained for mutually adjacent strips along a section of the rail track. These signals are then processed to determine total magnetic flux leakage for that section of track.

The signals are obtained by initially magnetising the section of rail for example by running a permanent magnet over the section of rail to induce a remnant magnetic field and subsequently passing one or a plurality of sensors along the track where each sensor produces a signal indicative of magnetic flux leakage. Thus the magnetising and the sensing are conducted at different times. The permanent magnet and the sensors are not supported on the same structure and run along the rail section at the same time. A plurality of sensors can be arranged to sense magnetic flux leakage along adjacent transverse strips as they are run along the section of the track to acquire data for a predetermined width of the track. Whether there is only one sensor and thus one signal or a plurality of sensors and thus multiple signals, the signal(s) are processed to determine total remnant magnetic flux leakage.

The processing includes filtering the signal(s) for that section of track, calculating a maximum peak to peak differential for the signal(s), and integrating the maximum differential for all of the sensor(s) for that section of track. The integrated value is representative of the total remnant magnetic flux leakage or damage index of the section of track. Using the empirically determined relationship between remnant magnetic flux leakage and predicted crack depth, and knowing the total Remnant magnetic flux leakage (i.e., damage index) one can "look up" the predicted crack depth for that section of track.

The length of the section of track over which the total remnant magnetic flux leakage is determined may be varied in accordance with the characteristics and usage of the track.

For example, in some circumstances, the length of track over which total Remnant magnetic flux leakage is determined may be in the order of 500 mm to 1000 mm. In other circumstances, this length may be greater for example over 5 m, or less for example in the order of 250 mm.

Figures 1, 1A:
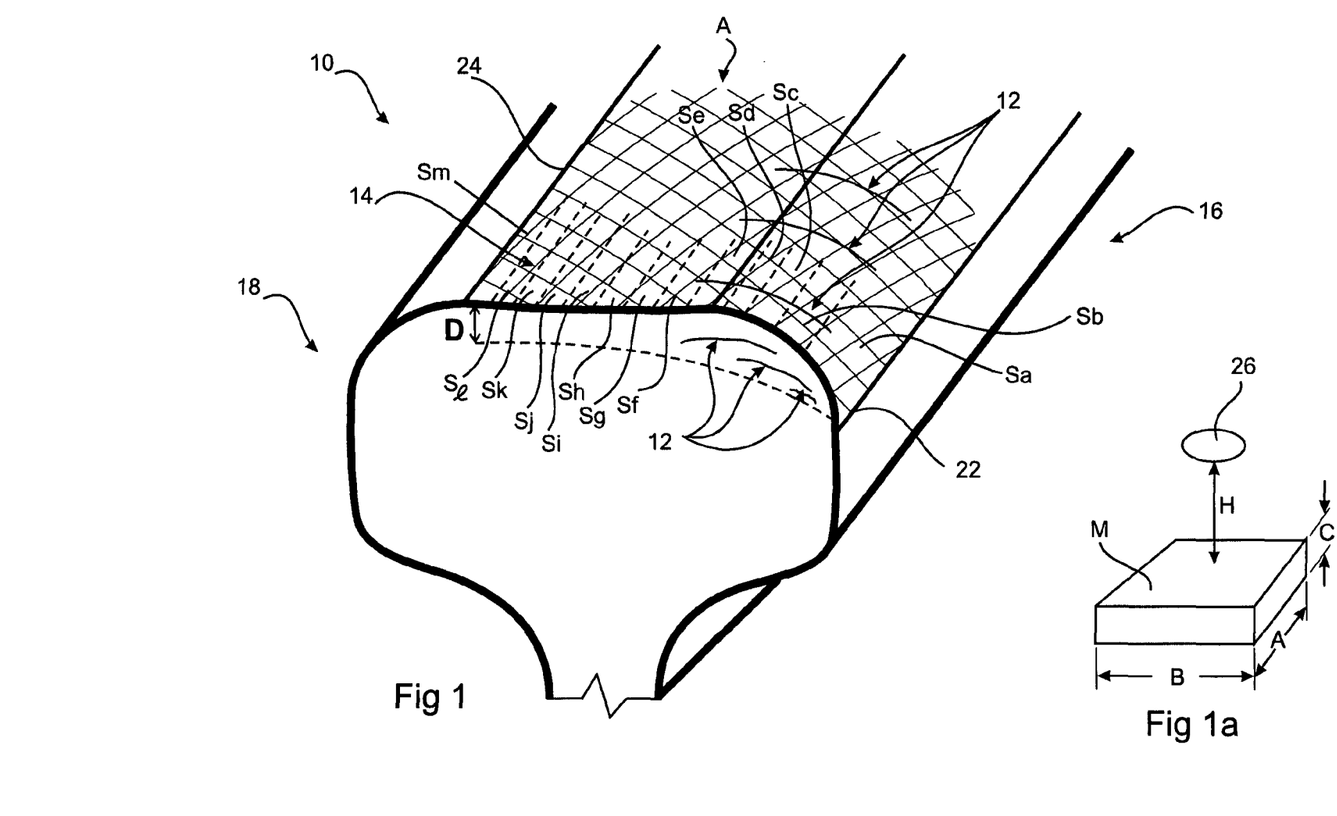
FIG. 1 is a schematic representation of a section of rail track to which an embodiment of the present method may be applied.
FIG. 1a is a representation of a model used for deriving a relationship between remnant flux and sensor height which is utilised in performing embodiments of the present method.

FIG. 1 illustrates a section of a rail track 10 in which cracks 12 have been caused by rolling contact fatigue. The cracks 12 have caused damage to a depth D from an outer surface 14 of the track 10. The right hand side of the track 10 is the gauge side 16 while the left hand side of the track 10 is the field side 18. The cracks 12 caused by rolling contact fatigue are initiated on the gauge side 16 and propagate toward the field side 18.

Figure 2:
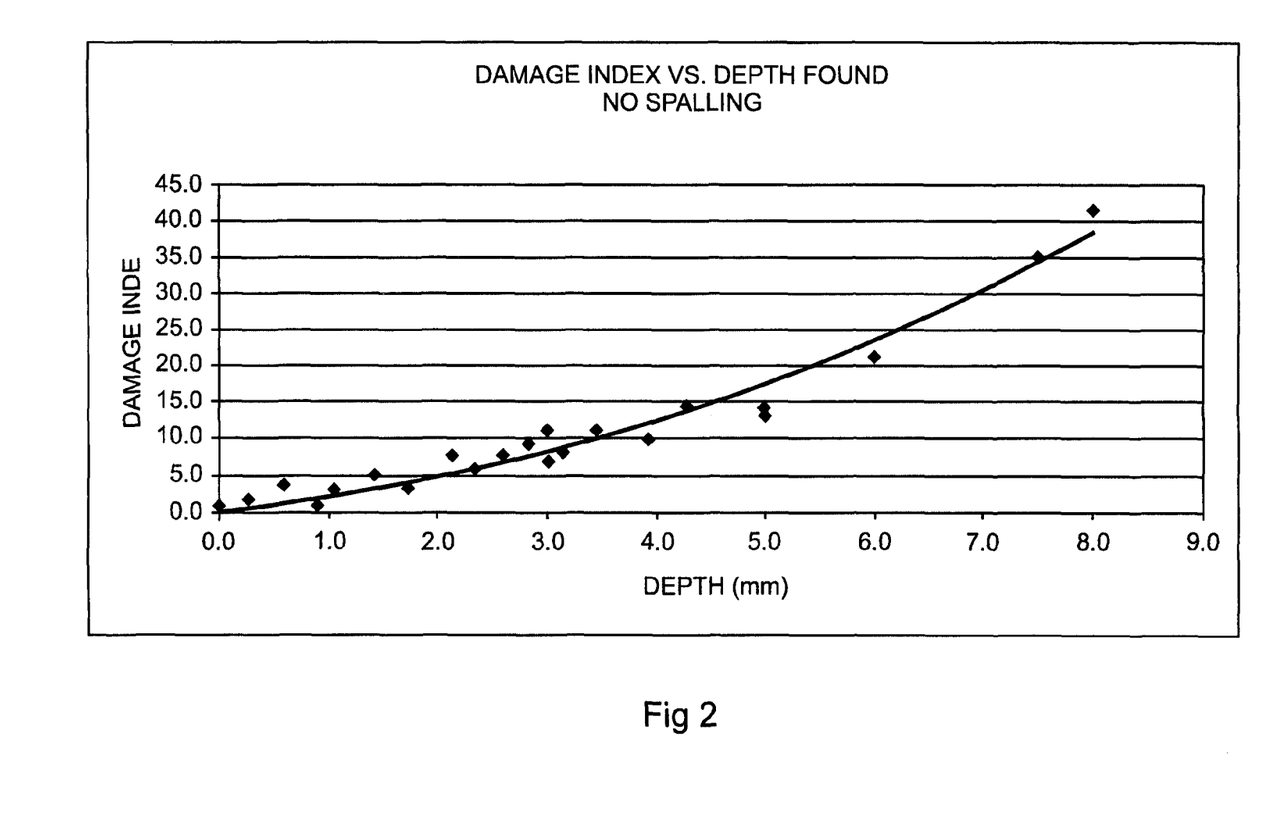
FIG. 2 graphically illustrates an empirically derived relationship between damage index of a section of rail, and depth of a crack in that section of rail.

Extensive testing by Applicant has revealed a strong relationship between the magnitude of flux signatures of crack damage and actual crack depth. This relationship was found by examination of sections of track in service which contained RCF damage. In brief, the sections of track were remove from a line in service and magnetised by passing a permanent magnet along the track section, leaving a remanent flux in the track sections after the passage of permanent magnet. The flux leakage from the remnant flux was then measured. The surface was then milled away by a known amount and the process repeated until no damage was present. The profile of the rail was taken into consideration for this calculation. This empirically determined relationship between damage index and crack depth is shown graphically in FIG. 2 where damage index plotted against damage (i.e. crack) depth. The damage index is in the units of Gauss.mm. In embodiments of the present method, the damage index is calculated using measurements of remnant flux leakage, then a graph of the type shown in FIG. 2 is used to provide a prediction of crack depth for a length of the track 10.

Embodiments of the present invention rely on the principle of remnant magnetic flux leakage. Non-magnetised ferrous materials contain magnetic domains which are randomly orientated. These materials can be magnetised by moving a magnet across a surface of articles made from such materials. The magnetic domains in the material are attracted to the magnet which causes them to align with the lines of magnetic flux of the magnet. When the magnet is removed, lines of magnetic flux remain in the article due to the aligned domains. This is known as remnant flux. If the article is free of defects, the flux travels undisturbed through the material. However defects support less flux than bulk material. When the flux paths encounter a defect, they cannot easily travel through the defect. This causes leakage of the flux at the location of the defect. The amount of flux leakage is related to the volume of the defect encountered.

In embodiments of the present invention, a magnet, typically a permanent magnet is run along the rail track 10 to induce a remnant flux in the rail 10. Assuming there are defects in the rail, there will be a leakage of this remnant flux which is detected by one or more sensors.

In an ideal scenario, the rail is magnetically saturated by the passing of the magnet. This reduces sensitivity in the measurement system to magnetising direction, magnet position, and height. However in most practical situations, very large rare earth magnets or high powered electro-magnets are required to magnetically saturate a section of track 10. In the absence of fully saturating a section of track 10, embodiments of the present invention contemplate inducing remnant magnetic flux in a section of rail 10 by use of relatively small permanent magnets that are run in one direction only on a section of track 10 to induce a remnant magnetic field in the section of track 10.

Once a magnetic field has been induced into the section of track, one or more sensors are run along the track in order to detect remnant magnetic flux leakage. One type of sensor that may be used for this is the Hall sensor. The Hall sensor works on the principle of Lorentz force. As an electric current is passed through the Hall sensor in the presence of a magnetic field normal to the current path the Lorentz force is generated. This causes the electric path to shift resulting in a charge separation across opposite faces of the Hall sensor. This produces a voltage which is proportional to the amount of magnetic flux.

Remnant magnetic flux leakage is sensed across a portion of the outer surface 14 constituting an area of interest A shown in cross hatch in FIG. 1. The area of interest A is bound longitudinally by a notional line 22 on the gauge side 16 of the track 10, and a notional line 24 near the field side 18 of the track 10. The area of interest A is the portion of the outer surface 14 which is most susceptible to RCF damage and where such damage is of most significant in terms of the longevity of the rail 10, and safety of an associated rail system.

Figure 3A:
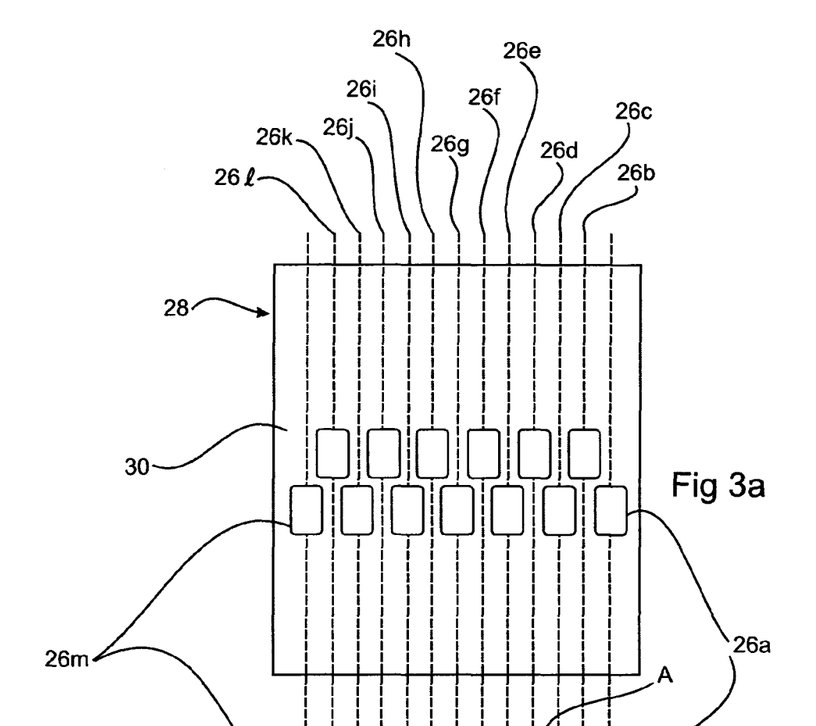
FIG. 3a is a bottom elevation of a sensor shoe used in an embodiment of the present method.
Figure 3B:
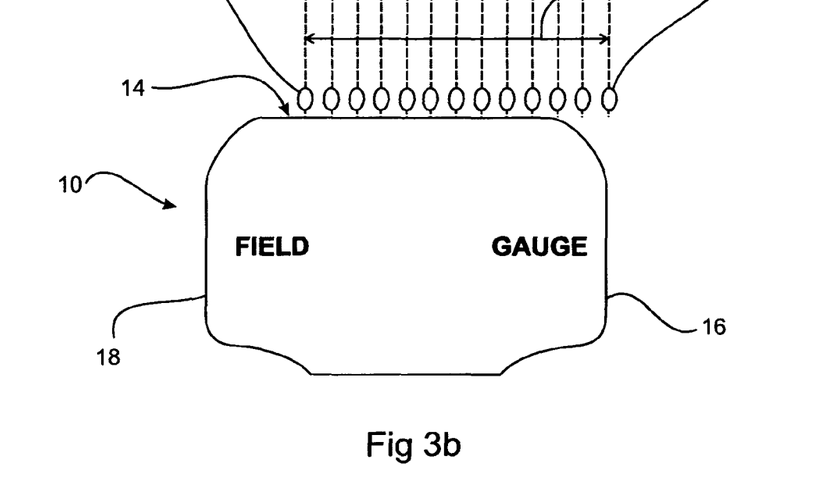
FIG. 3b illustrates the locations of sensors in the sensor shoe shown in FIG. 3a relative to a section of rail.

A Hall sensor is able to provide a reliable signal for a width substantially less than the transverse width of the area of interest A. Accordingly, a plurality of sensors is used in order to determine the remnant flux leakage over the area of interest A. An arrangement of sensors 26 is shown in FIGS. 3a and 3b. FIG. 3a illustrates a shoe 28 having a planar surface 30 which supports a plurality of (thirteen) sensors 26a-26m (hereinafter referred to in general as "sensors 26"). The sensors 26 are arranged in two transverse lines across the surface 30 of the shoe 28 in a staggered fashion. The staggering is merely a function of the physical size and shape of the sensors 26. This enables the sensors 26 to detect flux leakage in mutually adjacent transverse strips of the outer surface 14 as the shoe 28 is traversed along a length of the rail 10. FIG. 3b provides a representation of the relative locations of the sensors 26 across the area of interest A of the surface 14 of the rail 10.

In the present example, as there are thirteen sensors 26, the sensing of magnetic flux leakage from the rail 10 is made along thirteen mutually adjacent strips Sa-Sm (hereinafter referred to in general as "strips S") shown in FIG. 1. The transverse width of each strip S is the same, however due to the curvature particularly on the gauge side 16 of the rail 10, an arc length between adjacent strips is greater than the transverse distance between the strips.

The shoe 30 is held a constant distance from the outer surface 14 of the rail 10 by a trolley or other jig (not shown). The height of a particular sensor 26 above the corresponding strip S of the track 10 is of significance when processing the signals derived from the sensors 26. In particular, the amount of flux measured from the track 10 is dependent on the height H of the sensors 26 above the track 10. This relationship may be modelled by the following mathematical equation:

$$B = Br \frac{1}{\pi} \left[ \mathrm{ArcTan}\left(\frac{AB}{2H\sqrt{A^2 + B^2 + 4H^2}}\right) - \mathrm{ArcTan}\left(\frac{AB}{2(H+C)\sqrt{A^2 + B^2 + 4(H+C)^2}}\right) \right] \quad \text{(Equation 1)}$$

Where B is the measured flux at the sensor 26, Br is the remnant flux in the rail 10, and A, B and C relate to the geometry of the source of remnant flux, in this instance, the magnetic domains in the track 10 which give rise to the flux leakage. The magnetic domains are modelled as respective bar magnets M of dimensions A, B, C. FIG. 1a shows the relationship between the dimensions A, B, C of magnet M and the height H to a sensor 26. Testing by Applicant has determined that for a track 10 of a configuration shown in FIG. 1, A=80, B=4 and C=2.

When the shoe 28 is shaped to conform with the profile of the rail 10 so that the sensors 26 are maintained at a constant and uniform distance from the underlying strip S of the surface 14 then the signals derived from the sensors 26 are representative of the magnetic flux detected at a constant distance from the surface 14 transversely across the rail 10. However, if a flat shoe 28 as shown in FIG. 3 is used, it will be apparent that for example the sensor 26a is spaced at a greater distance from the underlying strip Sa than say the sensor 26k from the strip Sk. Accordingly, and as explained in further detail below, in this instance, the signals from the sensors 26 require height compensation to account for the reduction in magnetic flux with distance from the surface 14.

Figure 4:
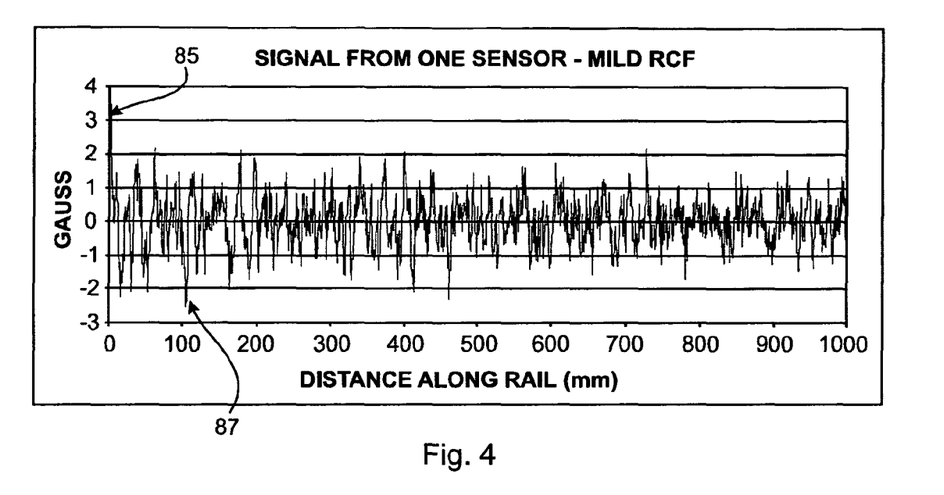
FIG. 4 is a graph illustrating the output of a sensor incorporated in the shoe shown in FIG. 3.

FIG. 4 depicts a typical signal from one sensor 26 along a 500 mm length of track 10. In the present embodiment, where thirteen sensors 26 are used, thirteen such signals are simultaneously produced as the shoe 30 is traversed along a section of the track 10. In order to provide a prediction of crack depth the signals from each sensor 26 is processed.

Figure 5:
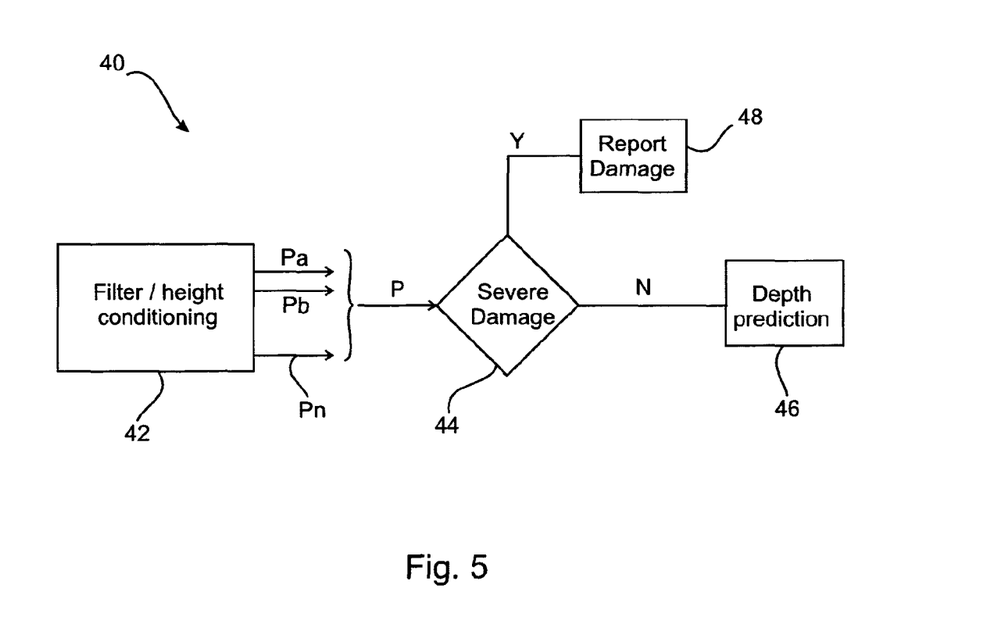
FIG. 5 is a flowchart depicting an embodiment of a method for predicting crack depth.

FIG. 5 broadly illustrates a method 40 of processing the signals from the sensors 26 to predict crack depth for a section of track 10. The method 40 comprises a first step 42 where the signals from the sensors 26 are filtered and compensated for height variations between the sensors and the surface 14 of the track 10. This produces an output processed signal P for each input sensor signal. In this example, as there are thirteen sensor signals, there will be thirteen processed signals Pa-Pm. At step 44, an assessment is made as to whether the processed signals indicate severe damage of the section of track 10. Severe damage is typically manifested in the form of a spall where a piece of the rail head has broken away from a surface 14. In the event that severe damage is not detected, the method 40 proceeds to step 46 where a prediction of crack depth is made by further processing the processed signals Pa-Pm. In the event that severe damage is detected, then the method 40 at step 48 issues a severe damage report. This report identifies the location of the section of track 10 containing the severe damage.

Figure 6:
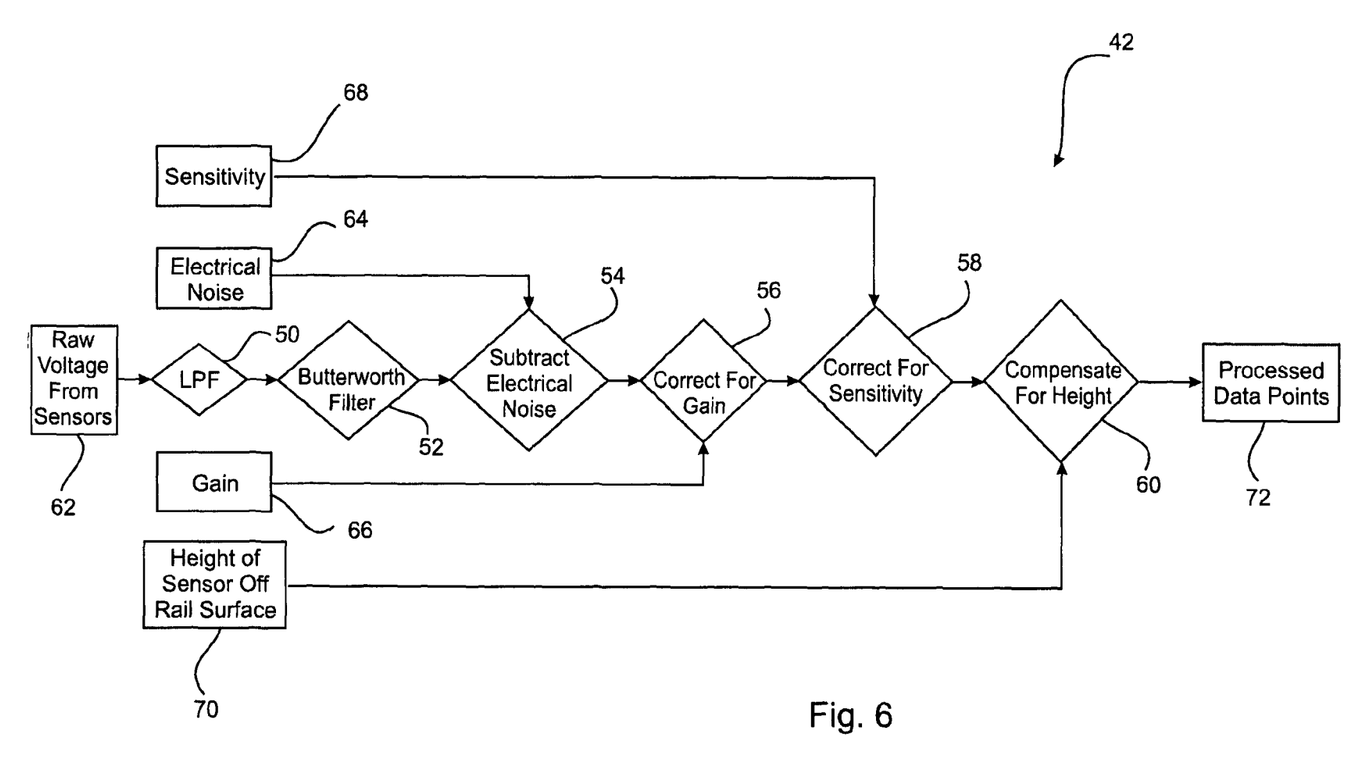
FIG. 6 is a flowchart illustrating in greater detail a filtering and height compensation step incorporated in the method shown in FIG. 5.

The steps 42, 44 and 46 are described in greater detail with reference to FIGS. 6, 7 and 8. FIG. 6 depicts the step 42 of filtering and height compensation of a signal from each of the sensors 26. The step 42 is conducted simultaneously but separately for each of the sensors 26. Step 42 comprises low pass filtering 50, high pass filtering 52, electrical noise compensation 54, gain correction 56, sensitivity correction 58, and height compensation 60. Respective inputs 62, 64, 66, 68 and 70 for steps 50 and 54-60 are also illustrated in FIG. 6.

Input 62 for the low pass filter step 50 is the raw voltage from a specific sensor 26. The raw voltage from each sensor 26 is sampled using distance based sampling. For example the sensor voltage may be sampled every 0.25 mm. This distance sampling rate is independent of speed of travel along the track. If speed of travel varies then the number of samples per second will vary. For example sampling every 0.25 mm at 2 km/h produces 2,222 samples per second while when travelling at 40 km/h 44,444 samples are produced per second. While the distance at which samples are taken can be changed for different applications, for any particular application it is fixed and independent of speed of travel. In contrast as demonstrated by the above example time domain sampling (i.e. number of samples per second) is dependant on the speed of travel. This has significance in terms of electrical noise which is based on time domain sampling. The low pass filter is a hardware filter which is configured to remove high frequency electrical noise. The cut-off frequency is dependant on the time based frequency of the samples. For this reason the cut-off frequency changes with speed. In the present embodiment the cut-off frequency is in order of one half the "time" sampling frequency.

After a signal from a sensor 26 has been low pass filtered at step 50, it then passes through a high pass software filter at step 52. It has been determined that the RCF damage typically produces flux signatures with a wavelength of <76 mm. Any features with wavelength longer than this are assumed to be "bulk" property features of the rail 10. The purpose of the high pass filtering at step 52 is to remove DC bias from the sensor voltage signals. In one embodiment, a $4^{th}$ order Butterworth High Pass Software Filter is used at step 52. The filtering is performed once in one direction and then in the reverse direction. Filtering in both directions compensates for phase distortion. In this regard, when applying the filter in a forward direction, the filter response for each data point is based on data points immediately before that data point. If the filter is run in the opposite (backwards) direction the data points are processed in the opposite direction meaning the data points immediately before the data point in question are different. This provides a different filter output. Running the filter forwards then backwards gives a symmetrical response. In practical terms, this enables the signals from the sensors 26 to be acquired by running the shoe 28 in any direction as an identical output will be derived from the filtering stage 52 regardless of the direction.

After the signal has been processed through the high pass filter at step 52, electrical noise is subtracted from the signal at step 54. The input 64 for step 54 is electrical noise. This noise is essentially the reading from a sensor 26 when in "air", i.e., outside of detecting distance of any magnetic flux.

Following step 54, the amplitude of the signal is subject to gain control or correction at step 56. This step takes account of the actual gain in the system. For example say the gain of the system is ten (i.e. ×10). This step converts the amplitudes to the actual sensor voltages and thus corrects for the system gain by, in this example, dividing the amplitudes by ten. Accordingly the input 66 is in effect a multiplier for the amplitude of the signal. A gain control of one tenth (i.e. ×1/10) is appropriate for the present embodiment.

Following the gain control step 56, the signal is subject to a Gauss conversion step 58. The sensitivity input 68 for step 58 is the sensitivity of the sensors, for example 0.04 v/gauss. This step converts the voltage derived from step 56 to Gauss by dividing that voltage by the sensitivity (i.e. the input 68). If sensors 26 are used with different sensitivity then that sensitivity is used as the input 68.

Following step 58, the signal undergoes a height conditioning or compensation step 60 to take account of the height or distance of the sensor 26 from the immediately underlying strip S of the track surface 14. The height conditioning step comprises multiplying the signal following processing at step 58 by the factor of:

$$= \frac{1}{\frac{1}{\pi}\left[\begin{array}{l}\operatorname{ArcTan}\left(\dfrac{AB}{2H\sqrt{A^2+B^2+4H^2}}\right)-\\ \operatorname{ArcTan}\left(\dfrac{AB}{2(H+C)\sqrt{A^2+B^2+4(H+C)^2}}\right)\end{array}\right]}$$

where, A=80, B=4, C=2 and H=the perpendicular height or distance of the sensor 26 from the rail surface 14. The constants A, B and C provided above are in relation to the application of the present method to a rail 10. For application of this method to either a rail of different configuration or alternately, a component of different shape or configuration such as a rail wheel or a steel beam, then these constants will be different. The height conditioning step 60 is applied irrespective of whether or not there is a variation in the distance between the sensors 26 and the underlying surface 14. When there is a variation in distance such as when a planar shoe as shown in FIGS. 3 and 9b is use, then this conditioning step is a height compensation step. When there is no distance variation, such as when a conformal shoe as shown in FIG. 9b is used so that each of the sensors 26 is spaced by the same distance from an underlying strip Sofa surface 14, the height conditioning step 60 simply multiplies every signal by the same constant.

The height conditioning step 60 is a dynamic step in that it is applied to the signals from the sensors 26 at every sampling point. This occurs to take account of variation in rail profile with distance. The rail profile varies from point to point along a track for many reasons including: non precise manufacture, distortions due to temperature, uneven wear, and different maintenance procedures at different locations. To facilitate the dynamic application of the height compensation step, at step 70 the actual height of the sensors 26 above the surface of the rail is measured at each sampling point. Such measurement may be carried out using various techniques and technologies, including ultrasonic or laser distance measurement. However it is envisaged that a laser based optical measurement system previously developed by Applicant and described in U.S. Pat. No. 7,492,448 may be used for this purpose. In any event which ever height measurement system is used, at step 70 the height H is measured for each sensor 26 and provided as an input to the compensation calculation occurring at step 60.

Depending on the construction of the conformal shoe it may be possible to take a height measurement once only, or to otherwise fixed the height H for all sensors 26 for every sampling point. In this regard a conformal shoe can be constructed which individually supports each sensor on a roller in contact with the rail where the roller is biased to follow the lengthwise profile of the rail. Thus as the shoe travels along the rail each sensor is physically held a constant height H from the rail surface. While this may obviate the need to dynamically apply step 70, in practice it is believe that use of the non conformal or planar shoe will enable the shoe to be traversed along the rail at a significantly greater speed than the conformal shoe.

Figure 9A:
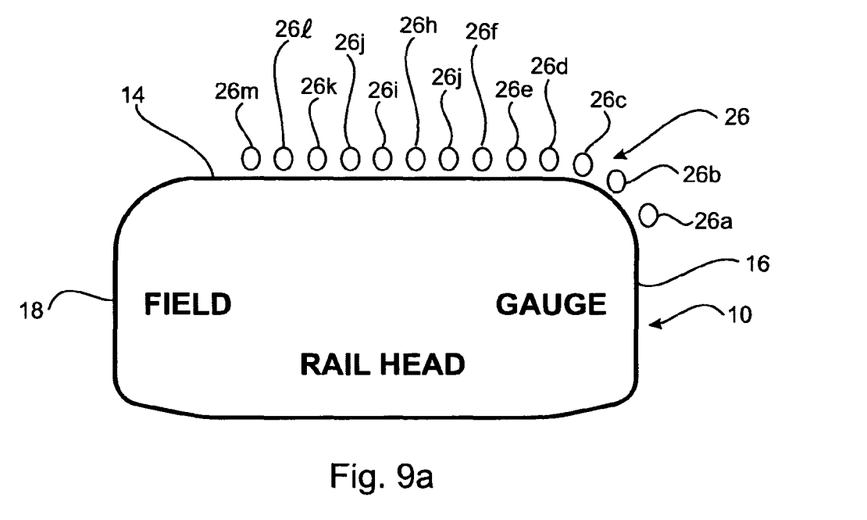
FIG. 9a is a schematic representation illustrating the relationship between sensors in a conformal shoe relative to a rail head for one embodiment of the present method.
Figure 9B:
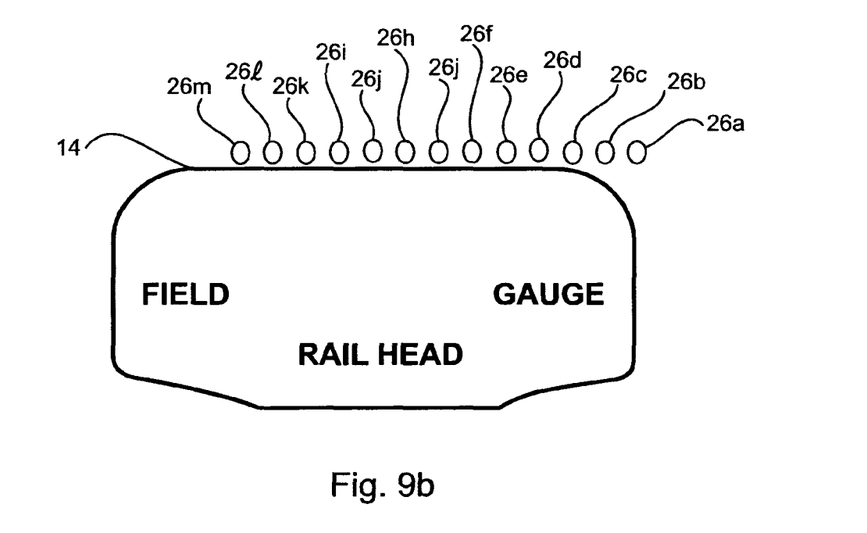
FIG. 9b represents a relationship between sensors in a planar shoe of the top shown in FIG. 3 with a rail head.

FIGS. 9b and 9a show the relative position of the sensors 26 to the surface 14 of the track 10 of a conformal shoe (FIG. 9a), and a planar shoe (FIG. 9b) of the type shown in FIG. 3. In one example the centres of sensors 26 are spaced by 5 mm. In the event that the sensors are wider than 5 mm this leads to a staggering of adjacent sensors 26 are shown in FIG. 3. It is apparent from FIG. 9b, that in the planar shoe, the height or distance between various sensors 26 and surface 14 of the rail 10 differs. In particular, the distance between the sensors 26a and 26b and the underlying surface 14 is different than for the remainder of the sensors 26c-26m. Thus when the planar shoe 28 is used to acquire the flux leakage height conditioning step 60 compensates for this variation in sensor to track surface distance.

The output from step 60 which also constitutes the output from step 42 comprises processed signals Pa-Pm which together form the input 72 for step 44

Figure 7:
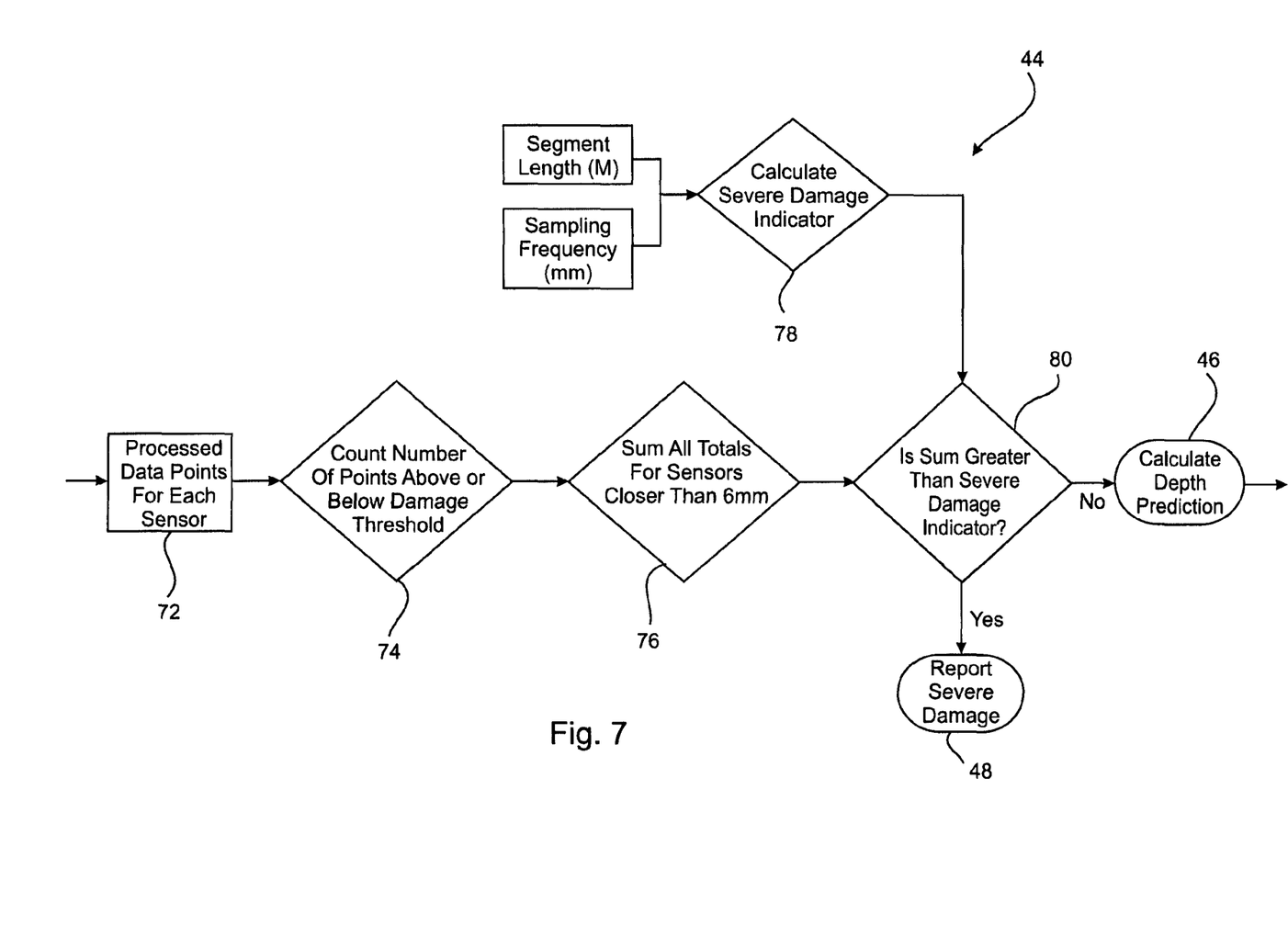
FIG. 7 is a flowchart illustrating in greater detail a severe damage assessment step incorporated in the method shown in FIG. 5.

FIG. 7 illustrates in greater detail the severe damage assessment step 44 depicted in FIG. 5. The purpose of step 44 is to determine whether the track 10 has a section with severe damage such as spalling. Severe damage is characterised by a low frequency high amplitude signal. Larger defects such as spalling will generate stronger dipoles in the material of the rail 10. The stronger dipoles will generate flux that exists over greater distances from the crack face. This means that major damage will display a lower frequency response than minor damage. The characteristics of low frequency and high amplitude are used in step 44 to determine the existence of severe damage.

Figure 10:
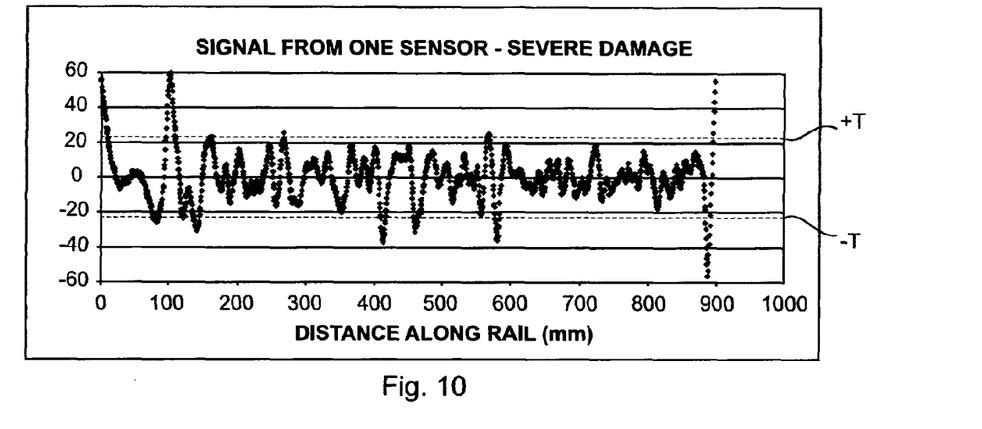
FIG. 10 is a representation of a sensor signal of the top shown in FIG. 4 after several stages of processing of the signal in accordance with embodiments of the method.

FIG. 10 illustrates a processed signal P used as one of the inputs 72 for the severe damage assessment step 44. The plot of the processed signal P shown in FIG. 10 illustrates a plurality of data points plotted as amplitude (Y axis) against distance (X), being distance along a section of track. In determining whether severe damage exists, separate counts are made of the number of data points for each signal P above and below the threshold amplitudes +/−T. Thus, with reference to FIG. 10, two counts are made, the first for data points above the threshold level +T, and the second for data points below the threshold −T. The counting of data points is illustrated as step 74 in FIG. 7. This count is made for each of the signals Pa-Pm. For the present embodiment the thresholds were empirically determined as +23.2 and −23.2.

At step 76 the total number (i.e. the sum) of points for all of the sensors Pa-Pm above the threshold +T(Σ+T) is determined together with the total number (sum) of points for all of the sensors Pa-Pm below the threshold −T(Σ−T). These sums are determined for each of the sensors Pa-Pm within a prescribed distance from the surface of the track 10. This distance in this embodiment is 6mm. If a sensor 26 is at a greater distance form the track surface its signal is disregarded.

At step 78, a severe damage indicator is pre-determined. For a section of rail 10, the severe damage indicator (SDI) is:

$$SDI = 35 \times \frac{\text{segment length (M)}}{\text{sampling frequency (MM)}}$$

where:
sampling length is the length of the portion of track under consideration, for example one metre; and,
sampling frequency is the sampling frequency of the voltage signals from the sensors 26, for example 0.25 mm.

At step 80, a comparison is made between the respective sums calculated at step 76 with the severe damage indicator calculated at 78. If:

Σ+T>SDI; or Σ−T>SDI

A severe damage report is generated at step 48 identifying the corresponding portion of track. This identification is relatively straight forward and calculated as a distance from a known starting point on the track 10 at which the sensing of magnetic flux commenced. As the starting point is known, and the length of each portion of track which is subject to the present method (for example, each portion being one metre in length) and given that the portions of the track are contiguous, a calculation can be made of the distance from the known starting point to the portion of track which has the reported severe damage.

Figure 8:
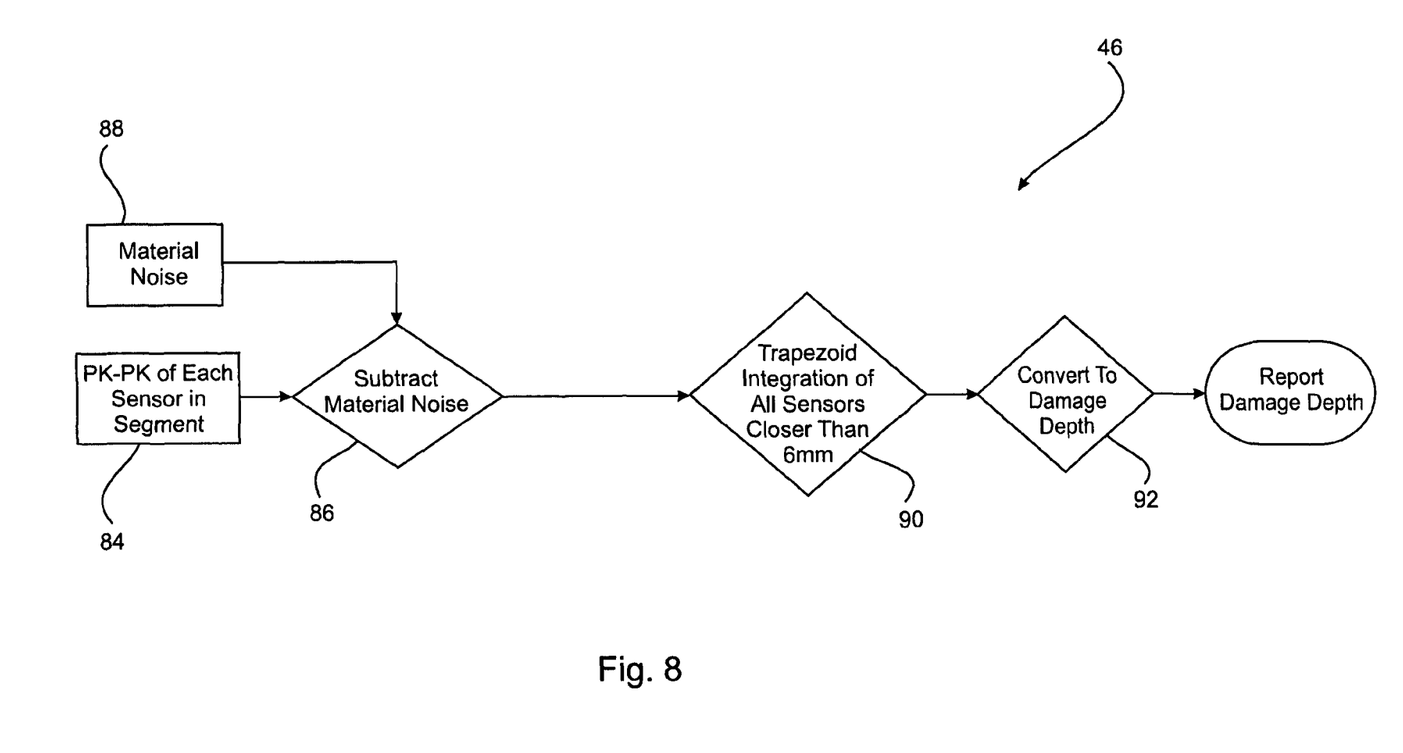
FIG. 8 is a flowchart depicting in greater detail a damage depth prediction step incorporated in the method shown in FIG. 5.

If at step 80, neither Σ−T nor Σ−T exceed the SDI then the method proceeds to the damage depth prediction step 46 shown in detail in FIG. 8. Predicting the depth of damage or cracking is based on a principle that the amount of Remnant flux leakage is related to the total volume of the defect or crack. It is assumed the Remnant flux detected by all of the sensors 26 is related to the geometry of the damaged article (in this instance rail 10). The flux is calculated for each specified section length (eg, one metre) of track 10. Over this length, the signals from each of the sensors 26 are analysed. At step 84 the lowest and highest peaks over the specified section are determined for each sensor 26. These are then subtracted to give a peak-peak difference for each sensor for the section at hand. For example, with reference to FIG. 4, the highest peak is shown as 85 having a value of approximately 3.6 while the lowest peak 87 is −2.6. Thus the difference between the highest and lowest peak for the signal over the portion of track is 3.6−(−2.6)=6.2.

As this process is using the peak values of the sensors the flux leakage is representative of the total flux leakage rather than being the actual total flux leakage.

Figure 11:
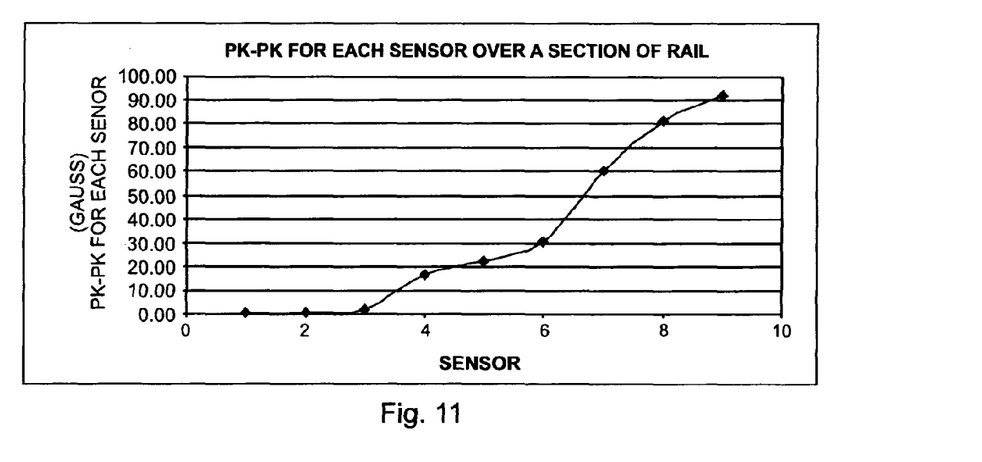
FIG. 11 graphically illustrates an integration stage in the processing of data in accordance with an embodiment of the present method; and, FIG. 12 illustrates a model of a crack or defect used in performing the present method.

At step 86 material noise is subtracted from each of the peak-peak values for each of the sensors 26. The material noise is provided as an input 88 and is the noise for the track 10 when there is no defect. The noise is the signal picked up by a sensor 26 when there is no crack or defect in the section of track 10. This is measured or empirically determined. For this embodiment the noise is empirically determined as 1.1 Gauss. At step 90, the noise corrected peak-peak signals for each sensor 26 is integrated. This step is illustrated graphically in FIG. 11. FIG. 11 depicts the noise corrected peak-peak value for each of sensor 26a-26m. The integration at step 90 is equivalent to calculating the area under the curve generated by a line joining the peak-peak outputs for each of the sensors 26. The integration provides the total flux leakage for a section of track 10.

Since the total flux leakage (i.e., the above integration) is calculated on the basis of the largest signals measured from each sensor, it represents a worse case prediction of damage depth.

Figure 12:
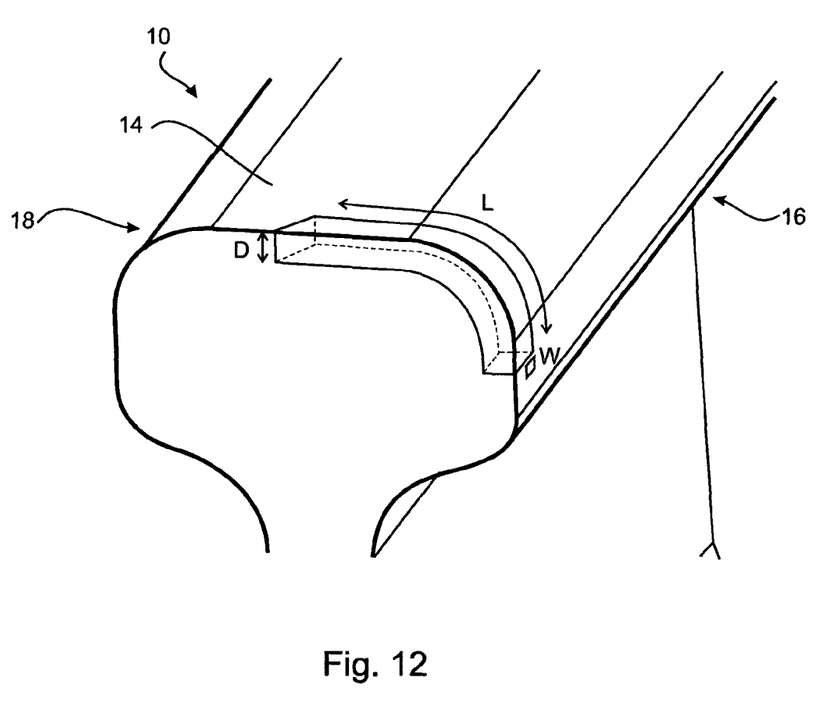

In the embodiment of the method 40 each defect or crack is analysed as a theoretical "shell-like" defect with a geometry WLD as shown in FIG. 12. This theoretical defect is assumed to be representative of a band of damaged material in the section of track 10. The dimension of D is the depth of the defect measured from the surface 14 of the rail 10, the dimension L is the transverse length of the defect and the dimension W is the width of the defect (ie, width at the mouth of a crack) measured in a direction of the length of the section of track 10.

Since the total flux is related to the geometry of the defect:

$$\text{TotalFluxOfDefect} = Br = f(W,L,D)$$

W is the crack mouth, which is known to be at least one order of magnitude smaller than L or D (W~0.005 mm, D~0.5 mm). As such, it is assumed to be negligible.

$$\Rightarrow Br = f(L,D)$$

It is also established that, for railway RCF defects, defect surface length (L) and depth of defect penetration into the rail or wheel (D) are related, thus total flux may be approximated as $$\Rightarrow Br = f(f(D),D) = f(D^2)$$

From this, it is predicted that the total flux (Br) measured from the ferrous specimen (typically a rail track or rail wheel) will be related to the depth of penetration of the damage (D).

Thus the present embodiment of the method of depth prediction is based on some assumptions which are unique to railway RCF damage. When embodiments of the method are used for different types of damage on other ferrous components these assumptions may require revision.

These assumptions are again summarised as follows.
1. The crack mouths are at least one order of magnitude below the crack length of depth.
2. RCF cracking exists as a band of damaged material over a section of rail in which all cracks grow similarly.
3. RCF crack surface length is proportional to depth of penetration.

In the case of spalling or surface voids, Assumption 1 is no longer valid. In this situation the present embodiment of the method will identify severe damage as being present, but will not report a damage depth prediction. This was described above with reference to both FIGS. 5 and 7 where in the case of severe damage the method proceeded to step 48 rather than damage prediction step 46.

When a section of track 10 has RCF damage manifested by one or more cracks, and the track is magnetised, adjacent crack faces will always have opposite polarity in order to maintain flux paths. As described above, each crack in effect acts as a source of magnetic flux. Adjacent opposite polarity sources will destructively interfere. When the defects are widely spaced (for example, greater than 8 mm), the destructive interference is negligible as signal strength from the source will decay at a rate of $1/R^2$ so that adjacent defects have little effect on each other. However, typically for RCF the cracks are more closely spaced for example, typically 2-8 mm so that destructive interference between cracks or defects does occur. Due to this interaction, it is possible for signals from very closely spaced defects to merge into one waveform. This means that very closely spaced defects will generate low frequency signals that correspond to many defects. On the other hand, widely spaced defects will generate individual signals for each defect, leading to higher frequency signals. Larger defects will generate stronger dipoles. Stronger dipoles generate flux that interferes with flux at great distances from the crack face. This means that severe or major damage will display at lower frequency response than minor damage, even if there is no signal interaction. The implications of this are that:

(a) Very closely spaced (<4 mm) major damage is represented by low frequency, high amplitude signals.
(b) Very closely spaced (<4 mm) minor damage is represented by low frequency, low amplitude signals.
(c) Widely spaced (>8 mm) major damage is represented by low frequency, very high amplitude signals.
(d) Widely spaced (>8 mm) minor damage is represented by high frequency, moderate to high amplitude signals.

From this, it is concluded that the total flux leakage or signature for a section of rail 10 (i.e., the damage index) will be dominated by the largest signal in it. This will either correspond to the largest defect or the most isolated defect. As the existence of a severe defect is reported prior to step 46 (and indeed if severe damage exists then step 46 is not conducted for that portion of track) the total flux calculated at step 90 is utilised to provide a prediction of damage/crack depth at step 92. This step involves using the sum or value resulting from the integration at step 90 as the damage index in the graph shown in FIG. 2 and from that damage index reading off a predicted crack depth. The predicted crack depth is the predicted crack depth for the most isolated defect in the section of track. It is not a predicted crack depth for every crack in the section or the sum of the individual crack depths for the section. The section of track 10 to which the crack prediction relates can be easily identified in the same manner as indicated above for the severe damage. The predicted crack depth may then be used by maintenance personnel to determine whether, and if so what, action is required for the corresponding section of track, e.g., no corrective action, grinding, or replacement.

The above embodiment of the present method is described in relation to prediction of crack depth in a rail track. However, it will be apparent to those skilled in the relevant arts; the method may equally be used to predict crack depth in other magnetisable materials and articles such as rail wheels, structural beams, columns, stringers and the like.

Modifications and variations in the above described embodiment that would be obvious to persons of ordinary skill in the art are deemed to be within the scope of the present invention.

The claims defining this invention are as follows:

1. A method of maintaining a magnetisable component in which cracks are induced due to fatigue, the method comprising:
    subjecting the magnetisable component to a magnetic field;
    after application of the magnetic field, determining a measure of remnant magnetic flux leakage for a section of the component;
    using the determined remnant magnetic flux leakage to calculate a damage index representative of a predicted crack depth for that section of the component; and
    dependent on the damage index, determining a maintenance action for that section of the component wherein the maintenance action is one of: taking no action; removing surface material from the section; and replacement of that section.

2. The method according to claim 1 further comprising: empirically determining a relationship between damage index and crack depth and utilising this relationship to predict crack depth for a calculated damage index.

3. The method according to claim 1 wherein determining remnant magnetic flux leakage comprises:
    obtaining at least one signal representative of remnant magnetic flux leakage at multiple sampling points along the section of the component and processing the at least one signal to determine remnant magnetic flux leakage.

4. The method according to claim 3 comprising applying a magnetic field in one direction along the section of the component to produce the remnant magnetic field in the section of the component and wherein the at least one signal is representative of magnetic flux leakage from the remnant magnetic field.

5. The method according to claim 4 wherein obtaining the at least one signal comprises obtaining respective signals for each of a plurality of mutually adjacent strips of the section of the component at each sampling point where the strips extend transverse to the direction of application of the magnetic field.

6. The method according to claim 3 wherein processing the at least one signal comprises filtering the at least one signal.

7. The method according to claim 6 wherein filtering the at least one signal comprises filtering the at least one signal through a high pass filter to remove signal components having a wavelength greater than a first wave length.

8. The method according to claim 7 wherein filtering the at least one signal comprises passing the at least one signal through a digital high pass filter in opposite directions.

9. The method according to claim 6 wherein the filtering comprises passing the at least one signal through a low pass filter to remove signals of a wavelength less than a second wave length.

10. The method according to claim 9 wherein the at least one signal is passed through the low pass filter prior to passing through the high pass filter.

11. The method according to claim 3 wherein processing the at least one signal comprises conditioning the signals on the basis of distance between each sensor and an underlying surface of the component for each of the sampling points.

12. The method according to claim 11 wherein conditioning the signal comprises multiplying each signal by a factor:

$$\frac{1}{\frac{1}{\pi}\left[\begin{array}{l}\operatorname{ArcTan}\left(\frac{AB}{2H\sqrt{A^2+B^2+4H^2}}\right)-\\ \operatorname{ArcTan}\left(\frac{AB}{2(H+C)\sqrt{A^2+B^2+4(H+C)^2}}\right)\end{array}\right]}$$

where A, B and C are constants dependant on the geometry of the component and H is the perpendicular distance of the or each sensor from the underlying surface of the component at each sampling point.

13. The method according to claim 12 wherein processing comprises analysing the one or more signals and providing an indication of major damage to the section of the component when the signals have a characteristic of low frequency and high amplitude.

14. The method according to claim 13, wherein providing an indication of major damage comprises subsequent to the high pass filtering, calculating respective sums of data points from the high pass filtered signals above and below respective positive and negative thresholds for all of the sensors, comparing the sums with a pre-calculated severe damage indicator, and reporting the existence of major damage when either sum exceeds the pre-calculated severe damage indicator.

15. The method according to claim 6 wherein processing further comprises calculating a maximum peak to peak amplitude for each filtered signal for the section of the component.

16. The method according to claim 15 wherein processing further comprises integrating the peak to peak amplitude for each signal for the section of the component to provide the measure of remnant magnetic flux leakage for the section of the component.

17. A method of maintaining a magnetisable component of a first geometry in which cracks are induced due to fatigue, the method comprising:
    subjecting the magnetisable component to a magnetic field;
    after application of the magnetic field, determining a measure of remnant magnetic flux leakage for a section of the component;

converting the remnant magnetic flux leakage to a predicted crack depth for that section of the component using an empirically determined relationship between remnant magnetic flux leakage and crack depth for a previously tested in service component of the first geometry; and dependent on the damage index, determining a maintenance action for that section of the component wherein the maintenance action is one of: taking no action; removing surface material from the section; and replacement of that section.

18. The method according to claim 17 wherein determining remnant magnetic flux leakage comprises:

obtaining at least one signal representative of remnant magnetic flux leakage at multiple sampling points along the section of the component and processing the at least one signal to determine remnant magnetic flux leakage.

19. The method according to claim 18 comprising applying a magnetic field in one direction along the section of the component to produce the remnant magnetic field in the section of the component and wherein the at least one signal is representative of magnetic flux leakage from the remnant magnetic field.

20. The method according to claim 19 wherein obtaining the at least one signal comprises obtaining respective signals for each of a plurality of mutually adjacent strips of the section of the component at each sampling point where the strips extend transverse to the direction of application of the magnetic field.

21. A method of magnetic crack depth prediction for a magnetisable component comprising:

determining a measure of remnant magnetic flux leakage for a section of the component by obtaining at least one signal representative of remnant magnetic flux leakage at multiple sampling points along the section of the component and processing the at least one signal to determine remnant magnetic flux leakage;

wherein processing the at least one signal comprises conditioning the at least one signals on the basis of distance between each sensor and an underlying surface of the component for each of the sampling points;

wherein conditioning the signal comprises multiplying the or each signal by a factor:

$$\frac{1}{\frac{1}{\pi}\left[\text{ArcTan}\left(\frac{AB}{2H\sqrt{A^2+B^2+4H^2}}\right)-\text{ArcTan}\left(\frac{AB}{2(H+C)\sqrt{A^2+B^2+4(H+C)^2}}\right)\right]}$$

where A, B and C are constants dependent on the geometry of the component and H is the perpendicular distance of the or each sensor from the underlying surface of the component at each sampling point; and, using the determined remnant magnetic flux leakage to calculate a damage index representative of a predicted crack depth for that section of the component.

22. The method according to claim 21 wherein processing comprises analysing the one or more signals and providing an indication of major damage to the section of the component when the signals have a characteristic of low frequency and high amplitude.

23. The method according to claim 22, wherein providing an indication of major damage comprises subsequent to the high pass filtering, calculating respective sums of data points from the high pass filtered signals above and below respective positive and negative thresholds for all of the sensors, comparing the sums with a pre-calculated severe damage indicator, and reporting the existence of major damage when either sum exceeds the pre-calculated severe damage indicator.

24. The method according to claim 21 wherein processing further comprises calculating a maximum peak to peak amplitude for each filtered signal for the section of the component.

25. The method according to claim 24 wherein processing further comprises integrating the peak to peak amplitude for each signal for the section of the component to provide the measure of remnant magnetic flux leakage for the section of the component.

* * * * *